United States Patent [19]

Sartorelli et al.

[11] Patent Number: 4,806,531
[45] Date of Patent: Feb. 21, 1989

[54] 2,3-BIS(AZIRIDINYL)-1,4-NAPHTHOQUINONE SULFONATE DERIVATIVES HAVING ANTINEOPLASTIC ACTIVITY

[75] Inventors: Alan C. Sartorelli, Woodbridge; Tai-Shun Lin, North Haven, both of Conn.

[73] Assignee: Yale University, New Haven, Conn.

[21] Appl. No.: 832,465

[22] Filed: Feb. 20, 1986

[51] Int. Cl.$^4$ .................... A61K 31/47; C07D 471/00
[52] U.S. Cl. .................................... 514/183; 514/314; 546/172; 548/963
[58] Field of Search ................ 548/963; 546/172; 514/183, 314

[56] References Cited

U.S. PATENT DOCUMENTS 4,233,215 11/1980 Driscoll et al. .................... 548/953

FOREIGN PATENT DOCUMENTS 1809762 11/1958 Fed. Rep. of Germany ...... 548/963

OTHER PUBLICATIONS

Wurm et al., Chem. Abstracts, vol. 101 (1984), entry 130363k.

Primary Examiner—Donald G. Daus
Assistant Examiner—C. Cseh
Attorney, Agent, or Firm—Ostrolenk, Faber, Gerb & Soffen

[57] ABSTRACT

The compounds of the formula:

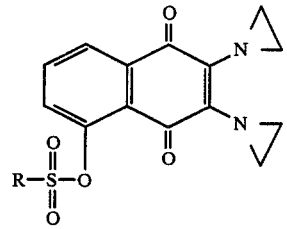

wherein R is selected from the group consisting of:
(a) a substituent having the formula:

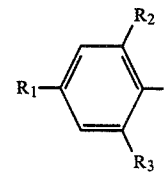

wherein $R_1$, $R_2$ and $R_3$ are each independently selected from the group consisting of hydrogen, alkyl of 1 to 6 carbon atoms, alkoxy of 1 to 4 carbon atoms, halogen and $-NO_2$,
(b) a substituent having the formula:

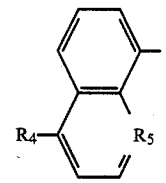

wherein $R_4$ is hydrogen or an $N(R')_2$ substituent, wherein $R'$ is an alkyl of 1 to 4 carbon atoms and $R_5$ is CH or N,
(c) alkyl of 1 to 18 carbon atoms,
(d) halo-substituted alkyl of 1 to 6 carbon atoms,
(e) styrenyl,
(f) toluenyl, or
(g) camphoryl.

The compounds have been found to have anti-neoplastic activity for use in inhibiting the growth of tumors.

26 Claims, No Drawings

2,3-BIS(AZIRIDINYL)-1,4-NAPHTHOQUINONE SULFONATE DERIVATIVES HAVING ANTINEOPLASTIC ACTIVITY

This research was supported in part by a grant (No. CH-211) from the American Cancer Society.

BACKGROUND OF THE INVENTION

1. Field of the Invention

This invention relates to compounds having antineoplastic activity, i.e., activity for inhibiting the growth of malignant tumors. More specifically it relates to compounds of the class 2,3-bis(aziridinyl)-1,4-naphthoquinone sulfonate derivatives, an intermediate therefor, and the use of these compounds in inhibiting malignant tumors.

2. Prior Art and Other Information

Assignee herein has discovered other classes of compounds useful for inhibiting the growth of malignant tumors. These compounds are described in U.S. Ser. No. 06/683,852, filed on Dec. 20, 1984, and now abandoned, and also in U.S. Ser. No. 06/810,644 now U.S. Pat. No. 4,684,747, filed on Dec. 18, 1985, which is a continuation-in-part of U.S. Ser. No. 06/683,852. The compounds described in this application are also described in Shyam et al. J. Med. Chem., 28, 525 (1985). These compounds are N,N'-bis(sulfonyl)hydrazines and are particularly active against both L1210 leukemia and B16 melanoma. Additionally, Assignee herein has also discovered 1-alkyl-2-arenesulfonyl-2-methoxycarbonyl sulfenyl hydrazines which are also useful for inhibiting the growth of malignant tumors. These compounds are described in U.S. Ser. No. 820,114 filed on Jan. 21, 1986, now abandoned and refiled in U.S. Ser. No. 142,354 on Dec. 28, 1987 and have significant activity against mice bearing the B16 melanoma.

Additionally, Applicant is aware of several references which describe compounds which might be considered relevant to the invention described and claimed herein.

In particular, U.S. Pat. No. 2,868,782 to Gauss describes polyhydro-2-aziridino-1,4-naphthoquinones. These compounds have the formula:

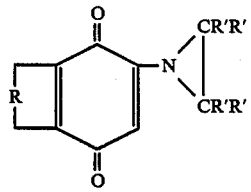

wherein R is a divalent radical selected from the group consisting of —CH$_2$CH$_2$CH$_2$CH$_2$—, —CH=CHCH$_2$CH$_2$— or —CH$_2$CH=CHCH$_2$— and R' may be hydrogen or methyl. The compounds are described as useful in chemotherapy and more particularly possessing cytostatic properties useful in the study and treatment of cancer.

U.S. Pat. No. 3,631,026 to Nakao describes 2,5-bis(1-aziridinyl)-1,4-benzoquinone derivatives of the formula:

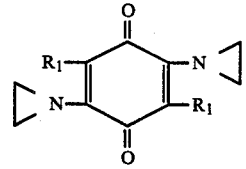

The compounds are said to exert an antileukemic activity and may be used on human beings as a drug for the remission and treatment of leukemia.

U.S. Pat. No. 4,146,622 to Driscoll describes aziridinyl quinone type compounds of the formula:

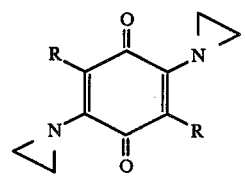

The preferred compounds are 2,5-diaziridinyl-1,4-benzoquinone derivatives.

U.S. Pat. Nos. 4,418,078 and 4,540,519 both to Murdock describes 1,4-bis(substituted-amino)-5,8-dihydroxyanthraquinone compounds of the type:

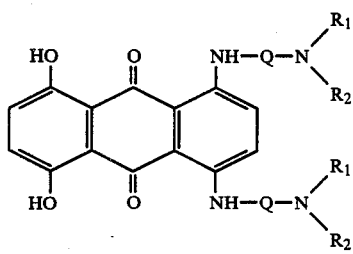

an aziridinyl substituent may be formed by R$_1$ and R$_2$. The compounds are said to be useful in inhibiting the growth of transplanted mouse tumors.

British Pat. No. 864,747 describes "alkyleneiminoquinones" of the formula:

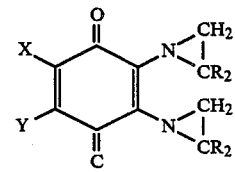

wherein X and Y may represent an "annelated pyridine or benzene nucleus" and R may be a hydrogen or methyl group. More specifically this reference describes "2,3-di-(ethylene-imino)-naphthoquinone-(1,4)". The compounds are described are capable of inhibiting the growth of animal tumor cells.

None of the foregoing references teach or suggest the compounds described and claimed herein.

OBJECTS AND SUMMARY OF THE INVENTION

An object of this invention is to provide a new class of compounds having antineoplastic activity.

A further object of this invention is to provide compositions containing such agents in a form suitable for administration to host organisms.

Still another object is to provide a method for preparing the novel compounds.

A further object is to provide novel compounds which have activity against malignant tumors.

The compounds of this invention have the formula:

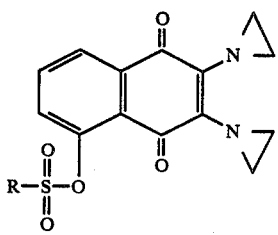

wherein R is selected from the group consisting of:
(a) a substituent having the formula:

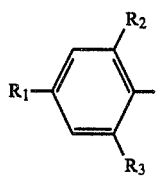

wherein $R_1$, $R_2$, and $R_3$ are each independently selected from the group consisting of hydrogen, alkyl of 1 to 6 carbon atoms, alkoxy of 1 to 4 carbon atoms, halogen and $-NO_2$,
(b) a substituent having the formula:

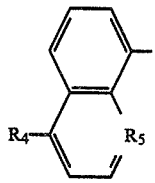

wherein $R_4$ is hydrogen or an $N(R')_2$ substituent, wherein $R'$ is an alkyl of 1 to 4 carbon atoms, and $R_5$ is CH or N,
(c) alkyl of 1 to 18 carbon atoms,
(d) halo-substituted alkyl of 1 to 6 carbon atoms,
(e) styrenyl,
(f) toluenyl, or
(g) camphoryl.

The compounds have been found to have pronounced antitumor activity. The compounds are particularly active against the L1210 leukemia and the B16 melanoma in tumor-bearing $CDF_1$ mice. In addition, they probably have low mammalian toxicity. The compounds may suitably be administered to host organisms internally in the form of conventional pharmaceutical preparations, for example, in conventional pharmaceutically acceptable enteral or parenteral excipients.

DETAILED DESCRIPTION OF THE INVENTION

The compounds described above are a new class of antineoplastic agents which have demonstrable effectiveness against the rodent tumors L1210 leukemia and B16 melanoma in $CDF_1$ mice.

As indicated above, the compounds have the general formula:

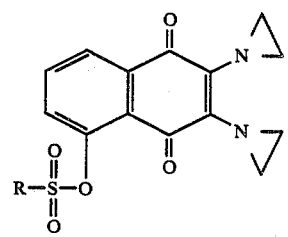

R may be selected from several substituents. The preferred substituents have the general formula:

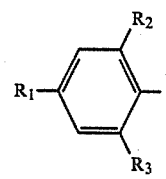

$R_1$, $R_2$ and $R_3$ may each be independently selected from the group consisting of hydrogen, alkyl of 1 to 6 carbon atoms, alkoxy of 1 to 4 carbon atoms, halogen and $-NO_2$. As used herein, and throughout the specification, the term "alkyl" represents straight or branched chain carbon atoms. Preferred alkyl substituents are methyl, ethyl, isopropyl and butyl.

Additionally as used herein and throughout the specification, the term "halogen" is meant to include all four halogens, namely, chlorine, bromine, iodine and fluorine. Chlorine and bromine are the preferred halogens.

The alkoxy substituent of 1 to 4 carbon atoms, includes straight or branched chain hydrocarbons thereon. A preferred alkoxy is methoxy.

Preferred compounds falling within the foregoing formula are:
(4) 2,3-Bis(aziridinyl)-5-(O-benzenesulfonyl)-1,4-naphthoquinone
(5) 2,3-Bis(aziridinyl)-5-[O-(p-toluenesulfonyl)]-1,4-naphthoquinone
(6) 2,3-Bis(aziridinyl)-5-[O-(p-methoxybenzenesulfonyl)]-1,4-naphthoquinone
(7) 2,3-Bis(aziridinyl)-5-[O-(p-t-butylbenzenesulfonyl)]-1,4-naphthoquinone
(8) 2,3-Bis(aziridinyl)-5-[O-(2',4',6'-trimethylbenzenesulfonyl)]-1,4-naphthoquinone
(9) 2,3-Bis(aziridinyl)-5-[O-(2', 4', 6'-tri-isopropylbenzenesulfonyl)]-1,4-naphthoquinone
(10) 2,3-Bis(aziridinyl)-5-[O-(p-chlorobenzenesulfonyl)]-1,4-naphthoquinone
(11) 2,3-Bis(aziridinyl)-5-[O-(p-nitrobenzenesulfonyl)]-1,4-naphthoquinone
(12) 2,3-Bis(aziridinyl)-5-[O-(2,4-dinitrobenzenesulfonyl)]-1,4-naphthoquinone In the foregoing formula, R may also be a substituent of the formula:

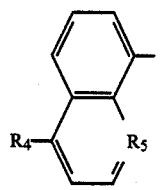

Preferred compounds of this formula are wherein $R_4$ is hydrogen or a $N(R')_2$ substituent, wherein $R'$ is an alkyl of 1 to 4 carbon atoms, and $R_5$ is CH or N. Preferred compounds of this type are the following:

(13) 2,3-Bis(aziridinyl)-5-[O-(naphthalene-1-sulfonyl)]-1,4-naphthoquinone

(14) 2,3-Bis(aziridinyl)-5-[O-(8-quinolenesulfonyl)]-1,4-naphthoquinone

(15) 2,3-Bis(aziridinyl)-5-[O-(5'-dimethylamino-1'-naphthalenesulfonyl)]-1,4-naphthoquinone.

Additionally preferred compounds are wherein R is a straight or branched chain alkyl of 1 to 18 carbon atoms, a halo-substituted alkyl of 1 to 6 carbon atoms, styrene, toluene, or camphor.

Preferred compounds of this type are:

(16) 2,3-Bis(aziridinyl)-5-(O-methanesulfonyl)-1,4-naphthoquinone

(17) 2,3-Bis(aziridinyl)-5-O-(butanesulfonyl)-1,4-naphthoquinone

(18) 2,3-Bis(aziridinyl)-5-[O-(1'-hexadecanesulfonyl)]-1,4-naphthoquinone

(19) 2,3-Bis(aziridinyl)-5-[O-(3-chloropropanesulfonyl)]-1,4-naphthoquinone

(20) 2,3-Bis(aziridinyl)-5-[O-(beta-styrenesulfonyl)]-1,4-naphthoquinone

(21) 2,3-Bis(aziridinyl)-5-[O-(alpha-toluenesulfonyl)]-1,4-naphthoquinone

(22) 2,3-Bis(aziridinyl)-5-[O-(d-10-camphorsulfonyl)]-1,4-naphthoquinone

The compounds of this invention of the formula:

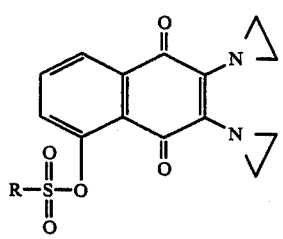

may be formed by reacting a compound of the formula:

with a compound of the formula:

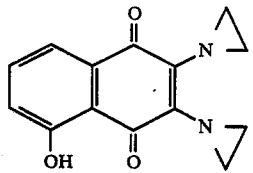

wherein R is as previously defined. More particularly, the appropriate sulfonylchloride is reacted with 2,3-bis-(aziridinyl)-5-hydroxy-1,4-naphthoquinone (Compound 2) in a solvent such as $CH_2Cl_2$, and further in the presence of a base, such as triethylamine. The resultant solution is then concentrated to a small volume and preferably chromatographed on a silica gel column to obtain the purified desired compound.

The 2,3-bis(aziridinyl)-5-hydroxy-1,4-naphthoquinone (Compound 2) is obtained by adding 2-aziridinyl-5-hydroxy-1,4-naphthoquinone (Compound 1) having the formula:

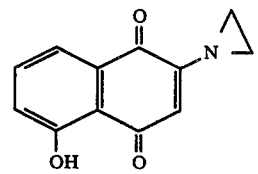

to ethylenimine with stirring. The excess ethylenimine is then removed by evaporation and the solid dissolved in $CH_2Cl_2$, washed and evaporated to dryness.

The 2-aziridinyl-5-hydroxy-1,4-naphthoquinone (compound 1) is produced by reacting 5-hydroxy-1,4-naphthoquinone with ethylenimine in an alcohol solvent, concentrated by evaporating the solvent, and then chromatographed on a silica gel column.

Optionally, instead of producing 2,3-bis(aziridinyl)-5-hydroxy-1,4-naphthoquinone (Compound 2) sequentially, 5-hydroxy-1,4-naphthoquinone may be reacted with at least 2 moles of ethylenimine to produce the 2,3-bis(aziridinyl)derivative. (See, British Pat. No. 864,747, incorporated herein by reference).

In producing compounds 1 and 2 herein, the reaction with ethylenimine may desirably be conducted by intimately contacting the starting naphthoquinone with ethylenimine in a suitable inert solvent. Any of those solvents that are inert and do not adversely affect the reaction of the process may be used. Suitable examples of such solvents which may be employed, include lower alkanols, e.g., methanol, ethanol, or isopropanol; di-lower alkyl ketones, e.g., acetone or methyl ketone. Preferred solvents are the lower alkanols, e.g., ethanol. The reaction temperature is not critical in the process, but it is usual and preferable to conduct the reaction at room temperature or below. Higher temperatures, may, of course, be applied although these do not result in any further advantages. The reaction period is not critical and may vary over a wide range mainly depending upon the kind of starting material employed. Usually it requires from several hours to several days to bring the reaction to completion.

To Applicant's knowledge the 2,3-bis(aziridinyl)-5-hydroxy-1,4-naphthoquinone (Compound 2) of the formula:

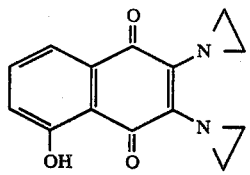

which is employed as an intermediate in the process for making the active claimed compounds, is a new chemical substance.

The compounds of this invention are preferably administered internally, in the form of conventional pharmaceutical preparations using a pharmaceutically acceptable carrier.

As used herein "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art.

Supplementary active ingredients can also be incorporated into the compositions, for example, conventional enteral or parenteral pharmaceutically acceptable excipients containing organic and/or inorganic inert carriers, such as water, gelatin, lactose, starch, magnesium stearate, talc, plant oils, gums, alcohol, vaseline, or the like. The pharmaceutical preparations can be in solid forms, for example, tablets, dragees, suppositories, capsules, or the like, or conventional liquid forms, such as suspensions, lotions, or the like. If desired, they can be sterilized and/or contain conventional pharmaceutical additives such as preservatives, stabilizing agents, wetting agents, emulsifying agents, buffers, or salts used for the adjustment of osmotic pressure. The pharmaceutical preparations may also contain therapeutically active materials.

The pharmaceutical preparation should include an amount of a compound of this invention effective for antineoplastic activity. The effective dosage will depend on the antineoplastic activity and toxicity of the particular compound employed, and is thus within the ordinary skill in the art to determine for any particular host mammal or other host organism. Suitable dosages may be, for example, in the range of about 0.5–15 mg/kg for man.

The tests herein indicate that the claimed Compounds of this invention possess excellent anti-tumor activity, resulting in a prolonged survival of test animals and curative effect on tumors.

SYNTHESIS AND PHYSICAL PROPERTIES
2-AZIRIDINYL-5-HYDROXY-1,4-NAPHTHOQUINONE

Compound 1

Ethylenimine (5.0 g, 115.7 mmol, 6 mL) in 60 mL of ethanol was added slowly to a stirred solution of 5-hydroxy-1,4-naphthoquinone (5.0 g, 28.7 mmol) in 940 mL of ethanol at 0° C. (ice-water bath) over a period of 0.5 hours. The solution was stirred for another 4 hours at the same temperature, and then concentrated in vacuo. The residue was chromatographed on a silica gel column (EtOAc-C$_6$H$_{14}$-CH$_2$Cl$_2$, 3:4:5, v/v) to afford 3.2 g (44%) of product.

The product physical properties were as follows:
mp 170°–172° C.; R$_f$ 0.57 (EtOAC-C$_6$-H$_{14}$-CH$_2$Cl$_2$, 3:4:5, v/v); NMR (CDCl$_3$) δ2.31 (s, 4H, 2-aziridinyl), 6.27 (s, 1H, 3-H), 7.23 (m, 1H, 6-H), 7.60 (m, 2H, 7- and 8-H), 11.92 (s, 1H, 5-OH, D$_2$O exchangeable). The product C$_{12}$H$_9$NO$_3$ should have C, 66.97; H, 4.22; N, 6.51. The product was found to have C, 67.21; H, 3.89; N, 6.18.

2,3-BIS(AZIRIDINYL)-5-HYDROXY-1,4-NAPHTHOQUINONE

Compound 2

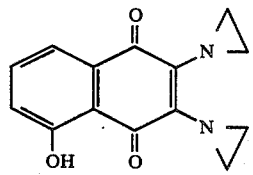

2-Aziridinyl-5-hydroxy-1,4-naphthoquinone (Compound 1) (1.0 g, 4.7 mmol) was added in small portions to 5.8 g (7 mL, 134.9 mmol) of ethylenimine at 0° C. with stirring. The reaction mixture was stirred at the same temperature for an additional 20 hours. The excess ethylenimine was removed in vacuo, and the resulting solid residue was redissolved in 150 mL of CH$_2$Cl$_2$. The solution was washed with water (3×20 mL) and dried (anhydrous Na$_2$SO$_4$). The drying agent was removed by filtration. The filtrate was evaporated to dryness under reduced pressure to give 1.1 g (92%) of product.

The product physical properties were as follows:
mp 181°–183° C.; R$_f$ 0.38 (EtOAc-C$_6$H$_{14}$, 1:1, v/v); NMR (CDCl$_3$) δ2.42 (s, 8H, 2- and 3-aziridinyl), 7.26 (d, 1H, 6-H), 7.48–7.54 (m, 1H, 7-H), 7.55 (d, 1H, 8-H), 12.16 (s, 1H, 5-OH, D$_2$O exchangeable). The product C$_{14}$H$_{12}$N$_2$O$_3$ should have C, 65.61; H, 4.72; N, 10.93. The product was found to have C, 65.40; H, 4.45; N, 11.26.

2-AZIRIDINYL-5-[O-(p-TOLUENESULFONYL)]-1,4-NAPHTHOQUINONE

Compound 3

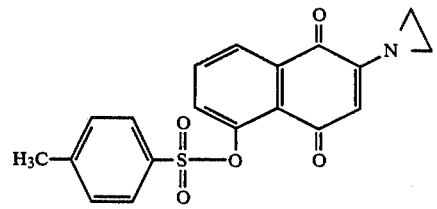

A solution of triethylamine (1.45 g, 14.4 mmol, 2 mL) and 1.20 g (6.30 mmol) of p-toluenesulfonyl chloride in 10 mL of CH$_2$Cl$_2$ was added to a solution of 0.70 g (3.25 mmol) of 2-aziridinyl-5-hydroxy-1,4-naphthoquinone (Compound 1) in 30 mL of CH$_2$Cl$_2$. The reaction mixture was stirred for 2 hours at room temperature. The solution was concentrated to a small volume and chromatographed on a silica gel column (EtOAc-C$_6$H$_{14}$-CH$_2$Cl$_2$, 2:3:5, v/v) to give 0.5 g (42%) of the desired product.

The product physical properties were as follows: mp 152°–154° C.; R$_f$ 0.48 (EtOAc-C$_6$H$_{14}$-CH$_2$Cl$_2$, 2:3:5, v/v); NMR (CDCl$_3$) δ2.26 (s, 4H, 2-aziridinyl), 2.47 (s, 3H, 4'-CH$_3$), 6.23 (s, 1H, 3-H), 7.36 (d, 2H, 3'- and 5'-H), 7.41 (d, 1H, 6-H), 7.66 (m, 1H, 7-H), 7.87 (d, 2H, 2'- and 6'-H), 8.07 (d, 1H, 8-H). The product, $C_{19}H_{15}NO_5S$·EtOAc should have C, 60.38; H, 4.63; N, 3.06. The product was found to have C, 60.74; H, 3.95; N, 3.02.

All of the compounds of the formula:

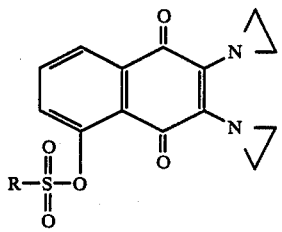

were synthesized in a manner similar to Compound 5 hereinafter, i.e., the R-sulfonyl chloride was reacted with 2,3-bis(aziridinyl)-5-hydroxy-1,4-naphthoquinone (Compound 2) in methylene chloride in the presence of triethylamine.

Synthesis of compounds of the formula:

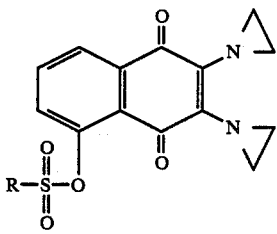

wherein R is:

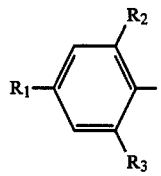

2,3-BIS(AZIRIDINYL)-5-[O-(p-TOLUENESULFONYL)]-1,4-NAPHTHOQUINONE

Compound 5

$R_1 = CH_3$; $R_2$ and $R_3 = H$

A solution of p-toluenesulfonyl chloride (0.50 g, 2.60 mmol) and triethylamine (0.73 g, 7.20 mmol, 1 mL) in 10 mL of $CH_2Cl_2$ was added to a stirred solution of 2,3-bis-(aziridinyl)-5-hydroxy-1,4-naphthoquinone (Compound 2) in 10 mL of $CH_2Cl_2$. The reaction mixture was stirred for another 20 hours at room temperature. The solution was then concentrated to a small volume and chromatographed on a silica gel column (EtOAc-$C_6H_{14}$, 1:1, v/v; and followed by EtOAc) to afford 0.2 g (41%) of product. The product had the following physical properties:
mp 157°-159° C.; $R_f$ 0.2 (EtOAc-$C_6H_{14}$, 1:1, v/v); NMR (CDCl$_3$) δ2.35 and 2.37 (two s, 8H, 2- and 3-aziridinyl), 2.45 (s, 3H, 4'-CH$_3$), 7.33 (d, 1H, 6-H), 7.35 (d, 2H, 3'- and 5'-H), 7.54 (dd, 1H, 7-H), 7.88 (d, 2H, 2'- and 6'-H), 8.01 (d, 1H, 8-H). The product $C_{21}H_{18}N_2O_5S$·0.5 EtOAc should have C, 60.78; H, 4.88; N, 6.16. The product was found to have: C, 60.29; H, 4.48; N, 5.99.

2,3-BIS(AZIRIDINYL)-5-(O-BENZENESULFONYL)-1,4-NAPHTHOQUINONE

Compound 4

$R_1 = R_2 = R_3 = H$

Physical Properties:
mp 154°-156° C.; $R_f$ 0.12 (EtOAc-$C_6H_{14}$, 1:1, v/v); NMR (CDCl$_3$) δ2.36 (two s, 8H, 2- and 3-aziridinyl), 7.32 (d, 1H, 6-H), 7.54-7.58 (m, 3H, 3'-, 5'- and 7-H), 7.69 (m, 1H, 5'-H), 8.01 (m, 3H, 2'-, 6'- and 8-H). The product $C_{20}H_{16}N_2O_5S$·0.25 $CH_2Cl_2$ should have C, 58.23; H, 3.98; N, 6.71. The product was found to have: C, 58.08; H, 3.92; N, 6.10.

2,3-BIS(AZIRIDINYL)-5-[O-(p-METHOXYBENZENESULFONYL)]-1,4-NAPHTHOQUINONE

Compound 6

$R_1 = OCH_3$; $R_2 = R_3 = H$

Physical properties:
mp 143°-145° C.; $R_f$ 0.47 (EtOAc-$CH_2Cl_2$, 1:1, v/v); NMR (CDCl$_3$) δ2.38 (s, 8H, 2- and 3-aziridinyl), 3.90 (s, 3H, 4'-CH$_3$O-), 7.01 (d, 2H, 3'- and 5'-H), 7.35 (d, 1H, 6-H), 7.57 (M, 1H, 7-H), 7.95 (d, 2H, 2'- and 6'-H), 8.02 (d, 1H, 8-H). The product $C_{21}H_{18}N_2O_6S$ should have C, 59.14; H, 4.25; N, 6.57. The product was found to have: C, 59.37; H, 4.25; N, 6.63.

2,3-BIS(AZIRIDINYL)-5-[O-(p-t-BUTYLBENZENESULFONYL)]-1,4-NAPHTHOQUINONE

Compound 7

$R_1 = C(CH_3)_3$; $R_2 = R_3 = H$

Physical properties:
mp 139°-141° C.; $R_f$ 0.39 (EtOAc-$C_6H_{14}$-$CH_2Cl_2$, 3:4:5, v/v); NMR (CDCl$_3$) δ1.36 (s, 9H, 4'-t-butyl), 2.36 (two s, 8H, 2- and 3-aziridinyl), 7.36 (d, 1H, 6-H), 7.58 (m, 3H, 3'-, 5'- and 7-H), 7.93 (d, 2H, 2'- and 6'-H), 8.02 (d, 1H, 8-H). The product $C_{24}H_{24}N_2O_5S$ should have C, 63.70; H, 5.35; N, 6.19. The product was found to have: C, 63.40; H, 5.53; N, 5.92.

2,3-BIS(AZIRIDINYL)-5-[O-(2',4',6'-TRIMETHYLBENZENESULFONYL)]-1,4-NAPHTHOQUINONE

Compound 8

$R_1 = R_2 = R_3 = CH_3$

Physical properties:
mp 125°-127° C.; $R_f$ 0.39 (EtOAc-$C_6H_{14}$, 1:1, v/v); NMR (CDCl$_3$) δ2.36 (s, 3H, 4'-CH$_3$), 2.39 (s, 8H, 2- and 3-aziridinyl), 2.61 (s, 6H, 2'- and 6'-CH$_3$), 7.02 (m, 3H, 3'-, 5'- and 6-H), 7.50 (t, 1H, 7-H), 8.00 (d, 1H, 8-H). The product $C_{23}H_{22}N_2O_5S$ should have C, 62.99; H, 5.06; N, 6.39. The product was found to have C, 62.69; H, 5.24; N, 6.04.

2,3-BIS(AZIRIDINYL)-5-[O-(2',4',6'-TRIISOPROPYLBENZENESULFONYL)]-1,4-NAPHTHOQUINONE

Compound 9

$R_1 = R_2 = R_3 = CH(CH_3)_2$

Physical properties:
mp 74°-76° C.; $R_f$ 0.37 (EtOAc-$C_6H_{14}$, 1:1, v/v); NMR (CDCl$_3$) δ1.22 (two s, 12H, 2'- and 6'-methyl of isopropyl), 1.30 (d, 6H, 4'-methyl of isopropyl), 2.38

(two s, 8H, 2- and 3-aziridinyl), 2.95 (m, 1H, 4'-CH of isopropyl), 4.08 (m, 2H, 2'- and 6'-CH of isopropyl), 6.96 (d, 1H, 6-H), 7.24 (s, 2H, 3'- and 5'-H), 7.50 (t, 1H, 7-H), 8.00 (d, 1H, 8-H). The product should have $C_{29}H_{34}N_2O_5S \cdot EtOAC$: C, 64.89; H, 6.93; N, 4.59. The product was found to have C, 64.46; H, 7.06; N, 4.16.

2,3-BIS(AZIRIDINYL)-5-[O-(p-CHLOROBENZENESULFONYL)]-1,4-NAPHTHOQUINONE

Compound 10

$R_1=Cl$; $R_2=R_3=H$

Physical properties:

mp 159°–161° C. dec; $R_f$ 0.57 (EtOAc-CH$_2$Cl$_2$, 1:1, v/v); NMR (CDCl$_3$) δ2.38 (two s, 8H, 2- and 3-aziridinyl), 7.38 (d, 1H, 6-H), 7.56 (d, 2H, 3'- and 5'-H), 7.61 (m, 1H, 7-H), 7.98 (d, 2H, 2'- and 6'-H), 8.04 (d, 1H, 8-H). The product $C_{20}H_{15}ClN_2O_5S$ should have C, 55.75; H, 3.51; N, 6.50. The product was found to have C, 56.60; H, 3.49; N, 5.99.

2,3-BIS(AZIRIDINYL)-5-[O-(p-NITROBENZENESULFONYL)]-1,4-NAPHTHOQUINONE

Compound 11

$R_1=NO_2$; $R_2=R_3=H$

Physical properties:

mp 150°–151° C. dec; $R_f$ 0.34 (EtOAc-C$_6$H$_{14}$, 1:1, v/v; NMR (CDCl$_3$) δ2.38 (two s, 8H, 2- and 3-aziridinyl), 7.45 (d, 1H, 6-H), 7.64 (t, 1H, 7-H), 8.08 (d, 1H, 8-H), 8.31 (d, 2H, 2'- and 6'-H), 8.44 (d, 2H, 3'- and 5'-H). The product $C_{20}H_{15}N_3O_7S \cdot 0.5$ EtOAc should have C, 54.43; H, 3.45; N, 8.66. The product was found to have C, 54.67; H, 3.31; N, 8.20.

2,3-BIS(AZIRIDINYL)-5-[O-(2,4-DINITROBENZENESULFONYL)]-1,4-NAPHTHOQUINONE

Compound 12

$R_1=R_2=NO_2$; $R_3=H$

Physical properties:

mp 164°–166° C. dec; $R_f$ 0.26 (EtOAc-C$_6$H$_{14}$, 1:1, v/v); NMR (CDCl$_3$) δ2.30 (s, 4H, 2-aziridinyl), 2.39 (s, 4H, 3-aziridinyl), 7.53 (d, 1H, 6-H), 7.69 (t, 1H, 7-H), 8.10 (d, 1H, 8-H), 8.59 (d, 1H, 6'-H), 8.63 (d, 1H, 5'-H), 8.72 (s, 1H, 3'-H). The product $C_{20}H_{14}N_4O_9S \cdot 0.5$ EtOAC should have C, 49.80; H, 3.42; N, 10.56. The product was found to have C, 50.20; H, 2.66; N, 10.24.

Synthesis and physical properties of Compounds:

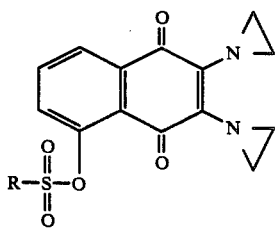

wherein R is:

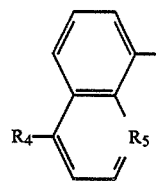

2,3-BIS(AZIRIDINYL)-5-[O-NAPHTHALENE-1-SULFONYL)]-1,4-NAPHTHOQUINONE

Compound 13

$R_4=H$; $R_5=CH$

Physical properties:

mp 118°–120° C.; $R_f$ 0.25 (EtOAc-C$_6$H$_{14}$-CH$_2$Cl$_2$, 3:4:5, v/v); NMR (CDCl$_3$) δ2.35 (s, 4H, 2-aziridinyl), 2.38 (s, 4H, 3-aziridinyl), 6.74 (d, 1H, 5'-H), 7.34 (m, 1H, 6'-H), 7.54 (m, 1H, 7'-H), 7.67 (m, 1H, 7-H), 7.78 (m, 1H, 3'-H), 7.95 (d, 1H, 6-H), 8.01 (d, 1H, 8-H), 8.13 (d, 1H, 4'-H), 8.18 (d, 1H, 8'-H), 8.90 (d, 1H, 1'-H). The product $C_{24}H_{18}N_2O_5S$ should have C, 64.56; H, 4.06; N, 6.28. The product was found to have C, 64.27; H, 4.07; N, 5.96.

2,3 BIS(AZIRIDINYL)-5-[O-8-QUINOLELESULFONYL)]-1,4-NAPHTHOQUINONE

Compound 14

$R_4=H$; $R_5=N$

Physical properties:

mp 161°–163° C.; $R_f$ 0.30 (EtOAc); NMR (CDCl$_3$) δ2.22 (s, 4H, 2-aziridinyl), 2.36 (s, 4H, 3-aziridinyl), 7.29 (d, 1H, 6-H), 7.51 (m, 1H, 3'-H), 7.57 (m, 1H, 6'-H), 7.70 (m, 1H, 7-H), 8.01 (d, 1H, 8-H), 8.19 (d, 1H, 4'-H), 8.31 (d, 1H, 5'-H), 8.55 (d, 1H, 2'-H), 9.05 (d, 1H, 7'-H). The product $C_{23}H_{17}N_3O_5S$ should have C, 61.73; H, 3.83; N, 9.39. The product was found to have C, 61.51; H, 3.74; N, 8.96.

2,3-BIS(AZIRIDINYL)-5-[O-(5'-DIMETHYLAMINO-1'-NAPHTHALENESULFONYL)]-1,4-NAPHTHOQUINONE

Compound 15

$R_4=N(CH_3)_2$; $R_5=CH$

Physical properties:

mp 79°–81° C. dec; $R_f$0.29 (EtOAc-C$_6$H$_{14}$; 7:3 v/v); NMR (CDCl$_3$) δ2.38 (two s, 8H, 2- and 3-aziridinyl), 2.92 [s, 6H, 5'-N(CH$_3$)$_2$], 6.71 (d, 1H, 6'-H). 7.26 (d, 1H, 6-H), 7.35 (dd, 1H, 7'-H), 7.51 (dd, 1H, 7-H), 7.66 (dd, 1H, 3'-H), 7.95 (d, 1H, 8'-H), 8.10 (d, 1H, 8-H), 8.54 (d, 1H, 4'-H), 8.65 (d, 1H, 2'-H). The product $C_{26}H_{23}N_3O_5S \cdot 0.5$ EtOAc should have C, 63.06; H, 5.10; N, 7.88. The product was found to have C, 62.64; H, 5.36; N, 8.64.

Synthesis and physical properties of Compounds of the formula:

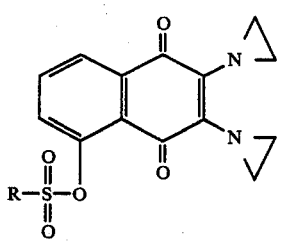

wherein R is: alkyl

2,3-BIS(AZIRIDINYL)-5-(O-METHANESULFONYL)-1,4-NAPHTHOQUINONE

Compound 16 R=CH₃ mp 171°–173° C.; $R_f$ 0.53 (EtOAc-CH₂Cl₂, 1:1, v/v); NMR (CDCl₃) δ2.42 (d, 8H, 2- and 3-aziridinyl), 3.45 (s, 3H, —SO₃CH₃), 7.59 (c, 1H, 6-H), 7.66 (m, 1H, 7-H), 8.06 (d, 1H, 8-H). The product $C_{15}H_{14}N_2O_5S$ should have C, 53.88; H, 4.22; N, 8.38. The product was found to have C, 53.59; H, 4.30; N, 8.27.

2,3-BIS(AZIRIDINYL)-5-O-(BUTANESULFONYL)-1,4-NAPHTHOQUINONE

Compound 17

R=CH₂CH₂CH₂CH₃

Physical properties:

Isolated as a glass, NMR (CDCl₃) δ1.02 (t, 3H, 4'-CH₃), 1.59 (m, 2H, 3'-CH₃), 2.05 (m, 2H, 2'-CH₂), 2.38–2.39 (two s, 8H, 2- and 3-aziridinyl), 3.59 (m, 2H, 1'-CH₂), 7.57 (d, 1H, 6-H), 7.62 (m, 1H, 7-H), 8.02 (d, 1H, 8-H). The product $C_{18}H_{20}N_2O_5S$·0.5 EtOAc should have C, 57.13; H, 5.75; N, 6.66. The product was found to have C, 57.26; H, 5.43; N, 6.22.

2,3-BIS(AZIRIDINYL)-5-[O-(1'-HEXADECANESULFONYL)]-1,4-NAPHTHOQUINONE

Compound 18

R=CH₂(CH₂)₁₄CH₃

Physical properties:

mp 71°–73° C.; $R_f$ 0.49 (EtOAc-C₆H₁₄, 1:1, v/v); NMR (CDCl₃) δ0.89 (t, 3H, 16'-CH₃), 1.27–1.30 (m, 22H, 5'- to 15'-CH₂), 1.40 (m, 2H, 4'-CH₂), 1.54 (m, 2H, 3'-CH₂), 2.07 (m, 2H, 2'-CH₂), 2.40 (s, 4H, 2-aziridinyl), 2.41 (s, 4H, 3-aziridinyl), 3.60 (t, 2H, 1'-CH₂), 7.60 (d, 1H, 6-H), 7.64 (t, 1H, 7-H), 8.04 (d, 1H, 8-H). The product $C_{30}H_{44}N_2O_5S$ should have C, 66.61; H, 8.14; N, 5.14. The product was found to have C, 66.76; H, 8.38; N, 5.00.

2,3-BIS(AZIRIDINYL)-5-[O-(3-CHLOROPROPANESULFONYL)]-1,4-NAPHTHOQUINONE

Compound 19

R=CH₂CH₂CH₂Cl mp 115°–117° C.; $R_f$ 0.22 (EtOAc-C₆H₁₄, 1:1, v/v); NMR (CDCl₃) δ2.41 (s, 8H, 2- and 3-aziridinyl), 2.61 (m, 2H, 2'-CH₂), 3.81 (m, 4H, 1'- and 3'-CH₂), 7.60 (d, 1H, 6-H), 7.65 (t, 1H, 7-H), 8.06 (d, 1H, 8-H). The product $C_{17}H_{17}ClN_2O_5S$·0.5 EtOAc should have been C, 51.76; H, 4.80; N, 6.36. The product was found to have C, 52.41; H, 4.58; N, 6.82.

2,3-BIS(AZIRIDINYL)-5-[O-(BETA-STYRENESULFONYL)]-1,4-NAPHTHOQUINONE

Compound 20

R=CH=CH—C₆H₅ mp 171°–173° C. dec; $R_f$ 0.24 (EtOAc-C₆H₁₄, 1:1, v/v); NMR (CDCl₃) δ2.37 (two s, 8H, 2- and 3-aziridinyl), 7.21 (d, 1H, styrene-H$_{alpha}$), 7.43–7.47 (m, 3H, 6-, 3'- and 5'-H), 7.25–7.56 (m, 3H, 2'-, 6'- and styrene-H$_{beta}$), 7.62–7.65 (m, 3H, 4'- and 7-H), 8.03 (q, 1H, 8-H). The product $C_{22}H_{18}N_2O_5S$·0.5CH₂Cl₂: C, 58.12; H, 4.12; N, 6.03. The product was found to have C, 57.76; H, 4.48; N, 5.71.

2,3-BIS(AZIRIDINYL)-5-[O-(alpha-TOLUENESULFONYL)]-1,4-NAPHTHOQUINONE

Compound 21

R=CH₂C₆H₅ isolated as a glass; $R_f$ 0.24 (EtOAc-C₆H₁₄, 1:1, v/v); NMR (CDCl₃) δ2.42 (s, 4H, 2-aziridinyl), 2.45 (s, 4H, 3-aziridinyl), 4.91 (s, 2H, alpha-CH₂), 7.43 (m, 3H, 3'-, 4'- and 5'-H), 7.51 (d, 1H, 6-H), 7.60 (m, 2H, 2'- and 6'-H), 7.61 (t, 1H, 7-H), 8.02 (d, 1H, 8-H). The product $C_{21}H_{18}N_2O_5S$ should have C, 61.45; H, 4.42; N, 6.83. The product was found to have C, 61.17; H, 4.30; N, 6.53.

2,3-BIS(AZIRIDINYL)-5-[O-(d-10-CAMPHORSULFONYL)]-1,4-NAPHTHOQUINONE

Compound 22

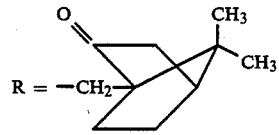

mp 121°–123° C.; $R_f$ 0.33 (EtOAc-C₆H₁₄; 1:1, v/v); NMR (CDCl₃) δ1.00 (s, 3H, 9'-CH₃), 1.21 (s, 3H, 8'-CH₃), 1.47 (m, 1H, 4'-H, a or e), 1.77 (m, 1H, 4'-H, a or e), 1.97 (m, 1H, 5'-H, a or e), 2.11 (m, 1H, 2'-H, a or e), 2.16 (m, 1H, 3'-H), 2.41 (s, 8H, 2- and 3-aziridinyl), 2.47 (m, 1H, 5'-H, a or e), 2.55 (m, 1H, 2'-H, a or e), 3.78 (d, 1H, 10'-H$_A$ or H$_B$), 4.05 (d, 1H, 10'-H$_A$ or H$_B$), 7.60 (d, 1H, 6-H), 7.65 (m, 1H, 7-H), 8.04 (d, 1H, 8-H). The product $C_{24}H_{24}N_2O_6S$ should have C, 61.52; H, 5.16; N, 5.98. The product was found to have C, 61.80; H, 5.42; N, 5.89.

SUMMARY TABLE I

| Compound | Formula | Melting Point (°C.) | Analysis |
| --- | --- | --- | --- |

SUMMARY TABLE I-continued

| 1 | [structure: 5-hydroxy-2-(aziridinyl)-1,4-naphthoquinone] | 170–172 | $C_{12}H_9NO_3$ |
|---|---|---|---|
| 2 | [structure: 5-hydroxy-2,3-bis(aziridinyl)-1,4-naphthoquinone] | 181–183 | $C_{14}H_{12}N_2O_3$ |
| 3 | [structure: tosylate of 2-aziridinyl naphthoquinone] | 152–154 | $C_{19}H_{15}NO_5S\cdot EtOAc$ |

Compounds of the formula:

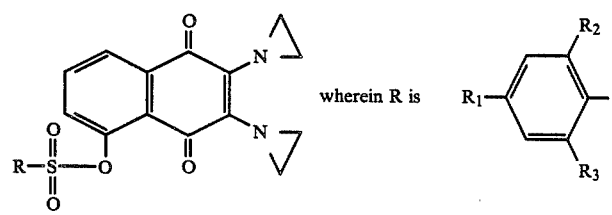

wherein R is:

| Compound | $R_1$ | $R_2$ | $R_3$ | Melting Point (°C.) | Analysis |
|---|---|---|---|---|---|
| 4 | H | H | H | 54–156 | $C_{20}H_{16}N_2O_5\cdot 0.25\ CH_2Cl_2$ |
| 5 | $CH_3$ | H | H | 157–159 | $C_{21}H_{18}N_2O_5S\cdot O.5\ EtOAc$ |
| 6 | $OCH_3$ | H | H | 143–145 | $C_{21}H_{18}N_2O_6S$ |
| 7 | $C(CH_3)_3$ | H | H | 139–141 | $C_{24}H_{24}N_2O_5S$ |
| 8 | $CH_3$ | $CH_3$ | $CH_3$ | 125–127 | $C_{23}H_{22}N_2O_5S$ |
| 9 | $CH(CH_3)_2$ | $CH(CH_3)_2$ | $CH(CH_3)_2$ | 74–76 | $C_{29}H_{34}N_2O_5S\cdot EtOAc$ |
| 10 | Cl | H | H | 159–161 | $C_{20}H_{15}ClN_2O_5S$ |
| 11 | $NO_2$ | H | H | 150–151 | $C_{20}H_{15}N_3O_7S\cdot 0.5\ EtOAc$ |
| 12 | $NO_2$ | $NO_2$ | H | 164–166 | $C_{20}H_{14}N_4O_9S\cdot 0.5\ EtOAc$ |

Compounds of the formula:

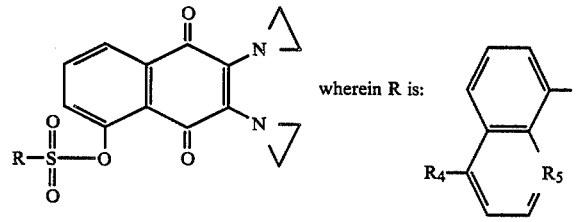

wherein R is:

| Compound | $R_4$ | $R_5$ | Melting Point (°C.) | Analysis |
|---|---|---|---|---|
| 13 | H | CH | 118–120 | $C_{24}H_{18}N_2O_5S$ |
| 14 | H | N | 161–163 | $C_{23}H_{17}N_3O_5S$ |
| 15 | $N(CH_3)_2$ | CH | 79–81 | $C_{26}H_{23}N_3O_5S\cdot 0.5\ EtOAc$ |

Compounds of the Formula:

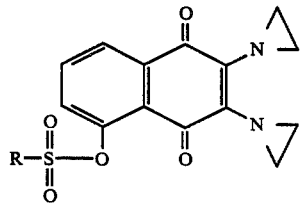

| Compound | R | Melting Point (°C.) | Analysis |
|---|---|---|---|

SUMMARY TABLE I-continued

| # | Structure | Melting Point | Analysis |
|---|---|---|---|
| 1 | (naphthoquinone with aziridine N, 5-OH) | 170–172 | $C_{12}H_9NO_3$ |
| 2 | (naphthoquinone with two aziridine N, 5-OH) | 181–183 | $C_{14}H_{12}N_2O_3$ |
| 3 | (tosylate-O-naphthoquinone with aziridine N) | 152–154 | $C_{19}H_{15}NO_5S\cdot EtOAc$ |

Compounds of the formula: 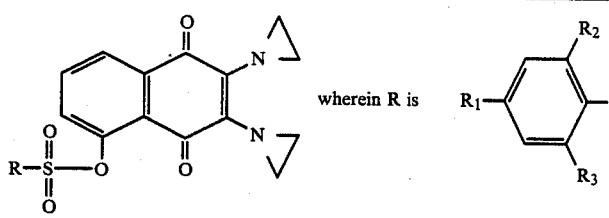 wherein R is:

| Compound | $R_1$ | $R_2$ | $R_3$ | Melting Point (°C.) | Analysis |
|---|---|---|---|---|---|
| 4 | H | H | H | 54–156 | $C_{20}H_{16}N_2O_5\cdot 0.25\,CH_2Cl_2$ |
| 5 | $CH_3$ | H | H | 157–159 | $C_{21}H_{18}N_2O_5S\cdot 0.5\,EtOAc$ |
| 6 | $OCH_3$ | H | H | 143–145 | $C_{21}H_{18}N_2O_6S$ |
| 7 | $C(CH_3)_3$ | H | H | 139–141 | $C_{24}H_{24}N_2O_5S$ |
| 8 | $CH_3$ | $CH_3$ | $CH_3$ | 125–127 | $C_{23}H_{22}N_2O_5S$ |
| 9 | $CH(CH_3)_2$ | $CH(CH_3)_2$ | $CH(CH_3)_2$ | 74–76 | $C_{29}H_{34}N_2O_5S\cdot EtOAc$ |
| 10 | Cl | H | H | 159–161 | $C_{20}H_{15}ClN_2O_5S$ |
| 11 | $NO_2$ | H | H | 150–151 | $C_{20}H_{15}N_3O_7S\cdot 0.5\,EtOAc$ |
| 12 | $NO_2$ | $NO_2$ | H | 164–166 | $C_{20}H_{14}N_4O_9S\cdot 0.5\,EtOAc$ |

Compounds of the formula: 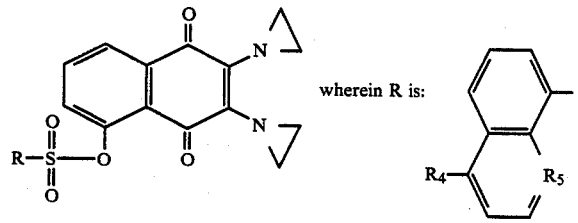 wherein R is:

| Compound | $R_4$ | $R_5$ | Melting Point (°C.) | Analysis |
|---|---|---|---|---|
| 13 | H | CH | 118–120 | $C_{24}H_{18}N_2O_5S$ |
| 14 | H | N | 161–163 | $C_{23}H_{17}N_3O_5S$ |
| 15 | $N(CH_3)_2$ | CH | 79–81 | $C_{26}H_{23}N_3O_5S\cdot 0.5\,EtOAc$ |

Compounds of the Formula: 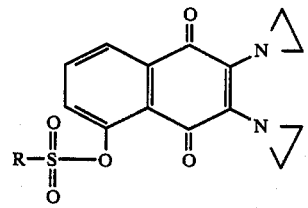

| Compound | R | Melting Point (°C.) | Analysis |
|---|---|---|---|

SUMMARY TABLE I-continued

| | | | |
|---|---|---|---|
| 16 | CH$_3$ | 171–173 | C$_{15}$H$_{14}$N$_2$O$_5$S |
| 17 | CH$_2$CH$_2$CH$_2$CH$_3$ | glass | C$_{18}$H$_{20}$N$_2$O$_5$S.0.5 EtOAc |
| 18 | CH$_2$(CH$_2$)$_{14}$CH$_3$ | 71–73 | C$_{30}$H$_{44}$N$_2$O$_5$S |
| 19 | CH$_2$CH$_2$CH$_2$Cl | 115–117 | C$_{17}$H$_{17}$ClN$_2$O$_5$S.0.5 EtOAc |
| 20 | CH=CH—C$_6$H$_5$ | 171–173 | C$_{22}$H$_{18}$N$_2$O$_5$S.0.5 CH$_2$Cl$_2$ |
| 21 | CH$_2$C$_6$H$_5$ | 171–173 | C$_{21}$H$_{18}$N$_2$O$_5$S |
| 22 | camphoryl | 121–123 | C$_{24}$H$_{24}$N$_2$O$_6$S |

BIOLOGICAL ACTIVITY OF COMPOUNDS

Transplantation of L1210 ascites cells was carried out by withdrawing peritoneal fluid from donor CDF$_1$ female mice bearing 7-day growths. The suspension was centrifuged for 2 minutes (1600 g), the supernatant peritoneal fluid was decanted, and a 10-fold dilution with isotonic saline was made. The cell number was determined with a Coulter particle counter and the cell population was adjusted to 10$^6$ cells/mL. One-tenth mL of the resulting cell suspension (containing approximately 10$^5$ cells) was injected intraperitoneally into each animal. The drug was administered by intraperitoneal injection beginning 24 hours after tumor implantation, once daily for 6 consecutive days. Test compounds were injected intraperitoneally as suspensions in isotonic saline in a volume of 0.25 mL. For any one experiment, animals were distributed into groups of five mice of comparable weight and maintained throughout the course of the experiment on Laboratory Chow pellets and water ad libitum. Controls given injections of a comparable volume of vehicle (saline) were included in each experiment. Mice were weighed during the course of the experiments, and the percentage change in body weight from onset to termination of therapy was used as an indication of drug toxicity. The results of these experiments are summarized in Table II.

TABLE II

THE EFFECTS OF 2,3-BIS(AZIRIDINYL)-1,4-NAPHTHOQUINONE SULFONATE DERIVATIVES ON THE SURVIVAL TIME OF MICE BEARING THE L1210 LUEKEMIA

| Compound | Daily dosage[a] (mg/kg) | Avg. Change in body wt. (%) | T/C × 100[b] |
|---|---|---|---|
| 1 | 5 | +12.7 | 94 (0/5) |
|   | 10 | +5.1 | 90 (0/5) |
|   | 15 | +2.1 | 94 (0/5) |
| 2 | 5 | +6.3 | 114 (0/5) |
|   | 10 | −3.2 | 96 (0/5) |
|   | 15 | −0.8 | 104 (0/5) |
| 3 | 20 | +7.3 | 102 (0/5) |
|   | 25 | +5.1 | 103 (0/5) |
|   | 30 | +1.2 | 111 (0/5) |
| 4 | 20 | −6.2 | — (5/5) |
|   | 25 | −8.3 | — (5/5) |
|   | 30 | −7.0 | 359 (4/5) |
| 5 | 20 | −2.2 | 155 (7/10) |
|   | 25 | −3.5 | 490 (9/10) |
|   | 30 | −7.4 | 248 (7/10) |
| 6 | 20 | −0.1 | 175 (1/5) |
|   | 25 | −2.4 | 222 (3/4) |
|   | 30 | −1.3 | 193 (2/5) |
| 7 | 20 | +12.0 | 104 (0/5) |
|   | 25 | +11.8 | 98 (0/5) |
|   | 30 | +6.7 | 98 (0/5) |
| 8 | 20 | −0.4 | 113 (0/5) |
|   | 25 | −2.5 | 113 (0/5) |
|   | 30 | −2.6 | 124 (0/5) |
| 10 | 20 | +4.2 | 161 (0/5) |
|   | 25 | +1.7 | 200 (0/5) |
|   | 30 | −2.7 | 167 (3/5) |
| 11 | 20 | −11.1 | 402 (4/5) |
|   | 25 | −12.9 | 293 (3/5) |
|   | 30 | −13.1 | 152 (4/5) |
| 15 | 20 | +2.2 | 110 (0/5) |
|   | 25 | +3.8 | 115 (0/5) |
|   | 30 | +3.9 | 117 (0/5) |
| 16 | 5 | +3.3 | 130 (0/5) |
|   | 10 | −7.1 | 185 (4/5) |
|   | 15 | −10.5 | 295 (2/5) |

[a]Drugs were administered by intraperitoneal injection, beginning 24 hr after tumor implantation, once daily for 6 consecutive days.
[b]T/C × 100 represents the ratio of the survival time of treated animals that died to control animals × 100. The average survival time of the untreated tumor-bearing control animals was 9.2 ± 0.4 days. The values in parentheses represent the number of mice that survived for greater than 50 days relative to the number of mice treated.

TABLE III

THE EFFECTS OF 2,3-BIS(AZIRIDINYL)-1,4-NAPHTHOQUINONE SULFONATE DERIVATIVES ON THE SURVIVAL TIME OF MICE BEARING THE B16 MELANOMA

| Compound | Daily dosage[a] (mg/kg) | Avg. Change in body wt. (%) | T/C × 100[b] |
|---|---|---|---|
| 4 | 50 | −1.3 | 156 |
|   | 100 | −12.3 | 180 |
|   | 150 | −13.5 | 148 |
| 5 | 50 | +4.5 | 144 |
|   | 100 | −1.9 | 153 |
|   | 150 | −9.8 | 141 |

[a]Drugs were administered by intraperitoneal injection, beginning 24 hr after tumor implantation, once daily for 6 consecutive days.
[b]T/C × 100 represents the ratio of the survival time of treated to control animals × 100. The average survival time of the untreated tumor-bearing control animals was 13.2 ± 1.2 days.

DISCUSSION OF EXAMPLES

The tumor-inhibitory properties of compounds 1–8, 10, 11, 15 and 16 were determined by measuring their effects on the survival time of mice bearing the L1210 leukemia. The results of tests conducted are summarized in Table II. Compounds 1–3 are not included within the claimed compounds which are active and, as indicated therein, did not display any substantial activity against the L1210 leukemia.

The inactivity of Compound 3 compared to the activity of Compound 5, indicates the criticality of the 2,3-bisaziridinyl substituents for providing antineoplastic activity.

Compounds 4 and 5 were also evaluated for anticancer activity against mice bearing the B16 melanoma. The results of these tests are summarized in Table III. Both of these compounds were found to be active against this tumor.

Although the invention has been specifically described with reference to particular embodiments, it is to be understood that the invention is not limited to the particulars disclosed and extends to all equivalents within the scope of the claims.

What is claimed is:

1. A compound of the formula:

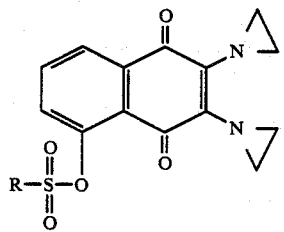

wherein R is selected from the group consisting of:
(a) a substituent of the formula:

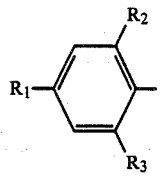

wherein $R_1$, $R_2$ and $R_3$ are each independently selected from the group consisting of hydrogen, alkyl of 1 to 6 carbon atoms, alkoxy of 1 to 4 carbon atoms, halogen and $-NO_2$, (b) a substituent of the formula:

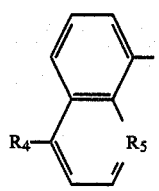

wherein R is hydrogen or an $N(R')_2$ substituent, wherein R' is an alkyl of 1 to 4 carbon atoms, and $R_5$ is CH or N, (c) alkyl of 1 to 18 carbon atoms,
(d) halo substituent alkyl of 1 to 6 carbon atoms,
(e) styrenyl,
(f) toluenyl, or
(g) camphoryl.

2. The compound of claim 1, wherein R is substituent (a) and $R_1$, $R_2$, and $R_3$ are hydrogen.

3. The compound of claim 1, wherein R is substituent (a) and $R_1$ is alkyl of 1 to 6 carbon atoms and $R_2$ and $R_3$ are hydrogen.

4. The compound of claim 3, wherein $R_1$ is methyl.

5. The compound of claim 3, wherein $R_1$ is tert-butyl.

6. The compound of claim 1, wherein R is substituent (a) and $R_1$ is alkoxy of 1 to 4 carbon atoms and $R_2$ and $R_3$ are hydrogen.

7. The compound of claim 6, wherein $R_1$ is methoxy.

8. The compound of claim 1, wherein R is substituent (a) and $R_1$, $R_2$ and $R_3$ are alkyl of 1 to 6 carbon atoms.

9. The compound of claim 8, wherein $R_1$, $R_2$ and $R_3$ are methyl.

10. The compound of claim 8, wherein $R_1$, $R_2$ and $R_3$ are isopropyl.

11. The compound of claim 1, wherein R is substituent (a) and $R_2$ and $R_3$ are hydrogen.

12. The compound of claim 11, wherein $R_1$ is $NO_2$.

13. The compound of claim 11, wherein $R_1$ is chlorine.

14. The compound of claim 1, wherein R is substituent (a) and $R_1$ and $R_2$ are $-NO_2$ and $R_3$ is hydrogen.

15. The compound of claim 1, wherein R is substituent (b) and $R_4$ is hydrogen and $R_5$ is CH or N.

16. The compound of claim 1, wherein R is substituent (b) and $R_4$ is dimethylamino and $R_5$ is CH.

17. The compound of claim 1, wherein R is a methyl substituent.

18. The compound of claim 1, wherein R is a butyl substituent.

19. The compound of claim 1, wherein R a hexadecyl substituent.

20. The compound of claim 1, wherein R is a 3-chloropropyl substituent.

21. The compound of claim 1, wherein R is a styrenyl substituent.

22. The compound of claim 1, wherein R is a toluenyl substituent.

23. The compound of claim 1, wherein R is a camphoryl substituent.

24. An antineoplastic composition comprising an antineoplastically effective amount of a compound of claim 1 and a pharmaceutically acceptable carrier.

25. A method of inhibiting the growth of L1210 leukemia and B16 melanoma tumors in host organisms which comprises administering to said host organism a tumor inhibitory amount of the compound of claim 1.

26. A compound of the formula:

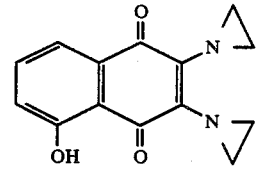

* * * * *